United States Patent [19]

Meilland

[11] Plant 4,681

[45] Apr. 7, 1981

[54] MINIATURE ROSE PLANT—MEICUBASI VARIETY

[75] Inventor: Marie L. Meilland, Antibes, France

[73] Assignee: The Conard-Pyle Company, West Grove, Pa.

[21] Appl. No.: 102,412

[22] Filed: Dec. 11, 1979

[30] Foreign Application Priority Data

Dec. 11, 1978 [DE] Fed. Rep. of Germany ..... ROS 278
Jan. 31, 1979 [DK] Denmark ..... 1002/79

[51] Int. Cl.[3] ..... A01H 5/00
[52] U.S. Cl. ..... Plt./10

[58] Field of Search ..... Plt./10

*Primary Examiner*—Robert E. Bagwill
*Attorney, Agent, or Firm*—Burns, Doane, Swecker & Mathis

[57] ABSTRACT

A new and distinct variety of rose plant of the Miniature Class having double flowers which are shiny velvety red currant red in color. The seed parent of the new variety was the variety Meidanu and the pollen parent was obtained by the crossing of the variety Meidacinu and the variety Duchess of Windsor.

17 Drawing Figures

SUMMARY OF THE INVENTION

The object of the present invention is to provide a new variety of rose plant of the Miniature Class having regular vegetation which is distinguished from prior varieties by the following characteristics:

(1) from a physical point of view, the plant with light green adult wood is bushy and produces double flowers of attractive form which are shiny velvety red currant red in color, the petals of which are consistent and possess a small whitish unguis on both faces; and (2) from a biological point of view has vigorous vegetation, abundantly forms flowers of long duration having petals which drop off cleanly, and average resistance to diseases.

In view of these characteristics the new variety meets the needs of the horticultural industry for all purposes, and particularly is suited for ornamentation in parks and gardens.

The new variety was created by artificial pollination whereby two genitors which previously had been studied for the possession of the characteristics sought in the new variety were combined.

The seed parent of the new variety Meidanu and the pollen parent was obtained by the crossing of the variety Meidacinu with the variety Duchess of Windsor.

The parentage of the new variety may be expressed as follows:

Meidanu × (Meidacinu × Duchess of Windsor)

The seeds resulting from the above pollination were sown and 304 plantlets were obtained which were physically and biologically different from each other. Selective study resulted in the identification of a single plant of the new variety. Extensive testing has confirmed the behavior and characteristics of the new variety. A miniature plant was produced having attractive unique red currant red flowers which are shiny velvety in appearance. Such flowers were formed in abundance and were found to be of long duration. The plant was particularly adapted for pot forcing and growing out-of-doors and exhibited regular vegetation.

The characteristics and properties of the new variety obtained as indicated above are strictly transmissible by asexual propagation, e.g. by grafting a bud eye. The rose plant of the new variety has been designated the Meicubasi variety.

BRIEF DESCRIPTION OF THE PHOTOGRAPH

The accompanying photograph shows as nearly true as it is reasonably possible to make the same in a color illustration of this color, typical specimens of plant parts of the new variety cultivated in the open air at Cannet des Maures, Var, France, illustrated in:

FIG. 1—a specimen of a young shoot;

FIG. 2—a specimen of inflorescence having four flowers wherein the sepals of three buds have not yet opened and the sepals of one bud have opened;

FIG. 3—a specimen of a bud at the opening of the sepals;

FIG. 4—a specimen of a bud at the opening of the petals;

FIG. 5—a specimen of a flower in the course of opening;

FIG. 6—a specimen of a flower—plan view—obverse;

FIG. 7—a specimen of a flower—plan view—reverse;

FIG. 8—a specimen of a fully opened flower—plan view—obverse;

FIG. 9—a specimen of a fully opened flower—plan view—reverse;

FIG. 10—a specimen of a receptacle showing the arrangement of the stamens;

FIG. 11—a specimen of a receptacle showing the arrangement of the pistils (stamens removed);

FIG. 12—a specimen of inflorescence having eight flowers wherein the resulting fruit is shown;

FIG. 13—a specimen of a floral stem;

FIG. 14—a specimen of a main branch;

FIG. 15—a specimen of leaf with three leaflets—upper surface;

FIG. 16—a specimen of leaf with five leaflets—under surface; and

FIG. 17—a specimen of leaf with seven leaflets—upper surface.

DETAILED DESCRIPTION

Figures 1, 2, 3, 4, 5, 6, 7, 8, 9, 10, 11, 12, 13, 14, 15, 16, 17:
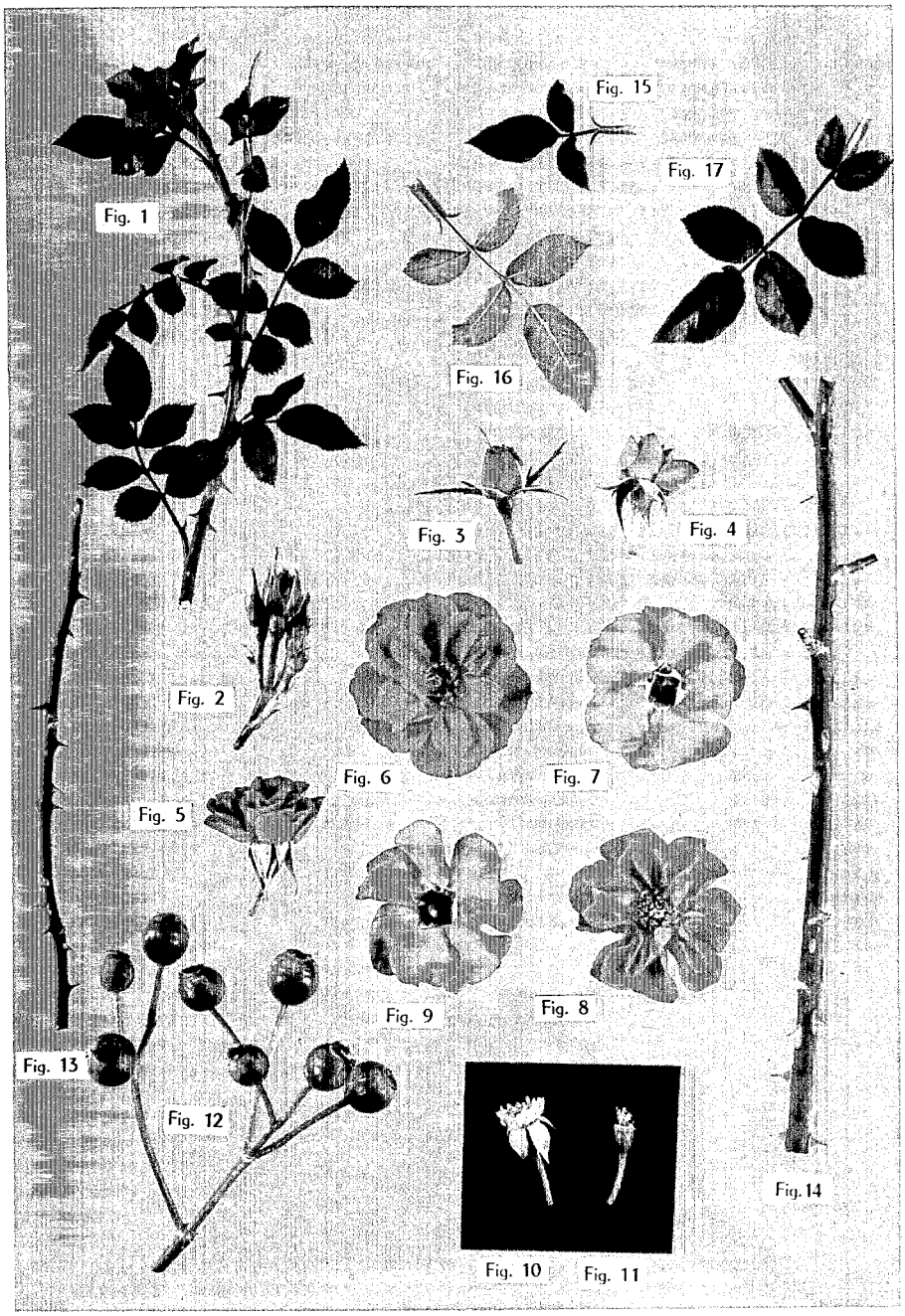

The plants described were grown in outdoor fields at the Cannet des Maures, Var, France.

The chart used in the identification of the colors is that of the Royal Horticultural Society (R.H.S. Colour Chart). The terminology preceding the numbered references has been added to designate in common terms, the corresponding colors.

Class: Miniature.

Plant:

*Height.*—50 cm. on average.

*Habit.*—Bushy.

Branches:

*Color.*—Young stems: Light green 146/B (yellow-green group), more or less shaded reddish. Mature wood: Light green 146/B (yellow-green group).

*Thorns.*—Shape: Upper edge: Straight, slender, lightly curved towards the base. Under edge: Concave. Size: Small. Quantity: Average. Color: On young stems: Reddish. On mature wood: Pinkish green then havana brown.

Leaves:

*Stipules.*—Adnate, pectinate; rather narrow and linear.

*Petioles.*—Upper surface: Grooved, reddish brown (young leaves), average green (adult leaves), with more or less glandular edges. Under surface: Light green. This side carries several small hooked thorns.

*Leaflets.*—Number: 3-5-7 (quite often). Shape: Elliptic. Serration: Single and regular. Texture: Leathery. General appearance: Leaves relatively ample, dense and semi-dull. Color: Young foliage: Upper surface: Dark green 147/A (yellow-green group). Under surface: Bronzish green 146/A (yellow-green group). Color: Adult foliage: Upper surface: Bronzish green 146/A (yellow-green group). Under surface: Light green 147/C (yellow-green group).

Inflorescence:

*Number of flowers.*—Commonly 3 to 21 multiflowers are present per stem, sometimes a uniflower is present.

*Peduncle.*—Straight, rigid, more or less spotted reddish brown, it is rather glandular and lightly tomentose. Length: 2.4 cm. on average.

*Sepals.*—Exterior surface: Tomentose, greenish, more or less spotted reddish. Interior surface: Light green, more or less spotted reddish and more or less glandular. The outside sepals have slightly appendicular sides.

*Bud.*—Shape: Prior to the opening of the sepals it is conical. Length: 1.4 cm. on average not counting the calyx when the sepals begin to open. Size: Medium. Color: At the point of opening: Interior surface: Cardinal red 53/A (red group), shiny velvety. Exterior surface: Cardinal red 53/A (red group), dull.

*Flower.*—Form: First hollow cup shaped, then opens to a flattened cup shape with visible stamens, double. Diameter: 5.5 cm. on average. Color: At point of opening: Upper surface: Red currant red 46/A (red group), shiny velvety. Under surface: Cardinal red 53/A (red group), dull. Color: During course of opening: Upper surface: Red currant red 46/A (red group), shiny velvety. Under surface: Cardinal red 53/B (red group), dull. Color: When fully open: Upper surface: Red currant red 46/A (red group), velvety flushed with cardinal red 53/B (red group). Under surface: Cardinal red 53/B (red group), dull color. Fragrance: None. Length of life of the bloom: Long. Corolla: Petals Texture: Leathery. Form: Rounded, becoming ovoid towards the center, cuneate base, have a small point and a small whitish unguis on both faces. Number: 30 on average as well as a few petals not completely formed at the center of the bloom. Stripping: They are easily detached. Pistils: Number: 61 on average. Stigmas: Normal, yellowish. Styles: Free, straw colored with light fuchsia top, more or less twisted and irregular in height. Receptacle: Light green, more or less spotted with reddish brown; at the point of the dehiscence of the anthers and in longitudinal section the receptacle is narrow and in the form of a jug.

Development:

*Vegetation.*—Very vigorous.

*Blossoming.*—Very abundant.

*Fruiting ability.*—Very good.

*Resistance to frost.*—Spring: Good. Winter: Good.

*Resistance to diseases.*—Very good.

I claim:

1. A new and distinct variety of Miniature rose plant characterized by the fact that:

from a physical point of view, the plant with light green adult wood is bushy and produces double flowers of attractive form which are shiny velvety red currant red in color, the petals of which are consistent and possess a small whitish unguis on both faces; and from a biological point of view has vigorous vegetation, abundantly forms flowers of long duration having petals which drop off cleanly, and average resistance to diseases;

substantially as shown and described.

* * * * *